United States Patent [19]
Mason

[11] Patent Number: 5,852,032
[45] Date of Patent: Dec. 22, 1998

[54] METHOD OF TREATING NICOTINE DEPENDENCE

[75] Inventor: Barbara J. Mason, Coconut Grove, Fla.

[73] Assignee: The University of Miami, Miami, Fla.

[21] Appl. No.: 752,955

[22] Filed: Nov. 20, 1996

Related U.S. Application Data

[60] Provisional application No. 60/006,962 Nov. 20, 1995.
[51] Int. Cl.$^6$ .................................................. A61K 31/485
[52] U.S. Cl. ........................................... 514/282; 514/813
[58] Field of Search ...................................... 514/282, 813

[56] References Cited

U.S. PATENT DOCUMENTS

| | | | |
|---|---|---|---|
| 4,946,848 | 8/1990 | Tuttle | 514/282 |
| 4,990,617 | 2/1991 | Boswell | 546/44 |
| 4,994,466 | 2/1991 | Sherman | 514/282 |
| 5,028,612 | 7/1991 | Glover | 514/282 |
| 5,057,322 | 10/1991 | Frost | 424/474 |
| 5,086,058 | 2/1992 | Sinclair | 514/282 |
| 5,552,406 | 9/1996 | Mendelson | 514/279 |
| 5,574,052 | 11/1996 | Rose | 514/343 |
| 5,593,684 | 1/1997 | Baker | 424/435 |

OTHER PUBLICATIONS

Malin et al., Psychopharmacology (1993), 112(2–3), 339–42.

Aceto et al., Nicotine's opioid and anti–opioid interactions: proposed role in smoking behavior, Eur. J. of Pharmacology, vol. 248, pp. 333–335, 1993.

Chiodera et al., Naloxone Decreases the Inhibiting Effect of Ethanol on the Release of Arginine–Vasopressin Induced by Cigarette Smoking in Man, Metabolism, vol. 36, No. 8, pp. 804–806, Aug. 1987.

Chiodera et al., Gamma–Aminobutyric Acid mediation of the Inhibitory Effect of Endogenous Opioids on the Arginine Vasopressin and Oxytocin Responses to Nicotine From Cigarette Smoking, Metabolism, vol. 42, No. 6, 762–765, Jun. 1983.

Corrigall et al., Opiate antagonists reduce cocaine but not nicotine self–administration, Psychopharmacology, vol. 104, pp. 167–170, 1991.

P.F. D'Arcy, Tobacco Smoking and Drugs: A Clinically Important Interaction, Drug Intelligence and Clinical Pharmacy, vol. 18, pp. 302–307, Apr. 1984.

Karras et al., Naloxone Reduces Cigarette Smoking, Life Sciences, vol. 27, pp. 1541–1545, 1980.

Little et al., Patterns of Multiple Substance Abuse During Pregnancy: Implications for Mother and Fetus, Southern Medical Journal, vol. 83, No. 5, pp. 507–509, May 1990.

Mason et al., A Double–Blind, Placebo–Controlled Pilot Study to Evaluate the Efficacy and Safety of Oral Nalmefene HCl for Alcohol Dependence, Alcohol Clin Exp Res., vol. 18, No. 5, pp. 1162–1167, 1994.

Nemeth–Coslett et al., Naloxone does not affect cigarette smoking, Psychopharmacology vol. 89, pp. 261–264, 1986.

O'Malley et al., Naltrexone and Coping Skills Therapy for Alcohol Dependence, Arch Gen Psychiatry, vol. 49, pp. 881–887, Nov. 1992.

Santiago et al., Opioids and breathing, J. Appl. Physiol., vol. 59, No. 6, pp. 1675–1685, 1985.

Seckl et al., Endogenous Opioids Inhibit Oxytocin Release During Nicotine–Stimulated Secretion of Vasopressin in Man, Clinical Endocrinology, vol. 28, pp. 509–514, 1988.

Volpicelli et al., Naltrexone in the Treatment of Alcohol Dependence, Arch Gen Psychiatry, vol. 49, pp. 876–880, Nov. 1992.

*Primary Examiner*—Phyllis G. Spivack
*Attorney, Agent, or Firm*—Cushman Darby & Cushman Intellectual Property Group of Pillsbury Madison & Sutro, LLP

[57] ABSTRACT

A method of treating a subject afflicted with nicotine dependence with the opiate antagonist, nalmefene is described. The subjects will not gain significant amounts of weight as a result of smoking reduction or cessation.

19 Claims, 1 Drawing Sheet

METHOD OF TREATING NICOTINE DEPENDENCE

This application claims the benefit of U.S. Provisional Appln. No. 60/006,962, filed Nov.20, 1995.

BACKGROUND OF THE INVENTION

Field of the Invention

The invention pertains to methods of treating human subjects suffering from nicotine dependence or addiction.

Description of the Prior Art

Nicotine dependence accounts for more mortality and morbidity in this country than does dependence on any other substance of abuse, including alcohol, cocaine and heroin. Thus, nicotine dependence represents an enormous cost to the American economy, in terms of health services and lost work days due to illness and premature death. Consequently, the development of safe and effective smoking cessation strategies is an important public health priority.

Current behavioral and somatic treatments for nicotine dependence, e.g., the nicotine patch, have limited efficacy in interrupting the chronic and relapsing course of the disorder. Moreover, existing treatments are associated with undesirable consequences. For example, *the New England Journal of Medicine* published a report on Nov. 2, 1995 of a nationwide survey of Americans over the age of 35 that found women who gave up smoking gained an average of 11 pounds and men 10 pounds. Such weight gain is a common reason for women, in particular, to return to cigarette smoking after an initial period of abstinence.

Several laboratory studies (Aceto et al., *Eur. Jour. Pharmacol.*, 248(4): 333–335 (1993); Chiodera et al., *Metabolism*, 36(8):167–170 (1987); Chiodera et al., *Metabolism*, 42(6):762–765 (1993); Corrigall et al., *Psychopharmacology*, 104(2):167–170 (1991); Karris and Kane, *Life Sci.*, 27:1541–1545 (1980); Nemeth-Coslett et al., *Psychopharmacology*, 89:261–264 (1986); and Seckl et al., *Clin. Endocrinol.*, 28(5) :509–514 (1988)) have used naloxone, a short-acting, intravenously-administered opiate antagonist that binds primarily to mu receptors, to examine an association between various biological and behavioral properties of nicotine dependence and the endogenous opiate system. The majority of studies support this association although Nemeth-Coslett et al. found naloxone did not significantly affect any measure of cigarette smoking in seven human volunteers during a sequence of two-hour laboratory sessions, and Corrigall and Coen found nicotine self-administration was not affected by the opiate antagonist naltrexone using a rodent model.

Nalmefene (6-methylene-6-desoxy-N-cyclopropylmethyl-14-hydroxydihydronormorphine) is a long-acting, orally available, potent narcotic antagonist with pure antagonist activity. Nalmefene binds more competitively to mu, delta and kappa receptors than naloxone and naltrexone, and unlike naltrexone, nalmefene has no dose-dependent association with liver toxicity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570), sudden infant death syndrome (U.S. Pat. No. 4,639,455), autoimmune diseases (U.S. Pat. No. 4,857,533), arthritic and inflammatory diseases (U.S. Pat. No. 4,863,928), interstitial cystitis (U.S. Pat. No. 4,877,791), allergic rhinitis (U.S. Pat. No. 4,880,813) and urticaria, various eczemas, and other mast cell-mediated dermatological disorders (U.S. Pat. Nos. 4,923,875 and 5,057,372).

In U.S. Pat. No. 5,086,058, a method is disclosed for treating alcoholism by extinguishing the alcohol-drinking response. This is accomplished by repeatedly administering nalmefene to a subject suffering from alcoholism and while the amount of nalmefene in the subject's body is sufficient to block the stimulatory effect of alcohol, having the subject drink an alcoholic beverage.

Nalmefene has not been studied in relation to nicotine dependence.

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457 and 4,478,840) and for treating shock (U.S. Pat Nos. 4,267,182 and 4,434,168), as well as for certain of the conditions cited above where nalmefene has been found useful. Naltrexone is commercially marketed as REVIA™ (DuPont) to treat alcohol dependency.

It may be preferred to combine nalmefene treatment with behavioral therapy to reduce nicotine dependence in afflicted subjects.

SUMMARY OF THE INVENTION

It is an object of the present invention to provide a method of treating human subjects afflicted with nicotine dependence which is safe and effective.

It is a further object of this invention to provide a method as aforesaid which may be practiced on an in-patient or out-patient basis.

It is yet another object of the present invention to provide a method as aforesaid wherein the subjects will not gain significant amounts of weight as a result of smoking reduction or cessation.

In keeping with this object and others that will become apparent hereinafter, the present invention resides, briefly stated, in a method of treating human subjects afflicted with nicotine dependence by administering to said subjects from about 10 to about 300 mg of nalmefene daily for a period of about seven days to about one year. In the case of certain subjects, the administration of nalmefene may be continued even longer than one year in accordance with the clinical assessment of the monitoring health personnel. Alternatively, the administration of nalmefene may be stopped for a period of time with the subject being observed for signs of continuing nicotine dependence, and the administration of nalmefene then resumed if necessary.

DETAILED DESCRIPTION OF THE INVENTION

Figure 1:
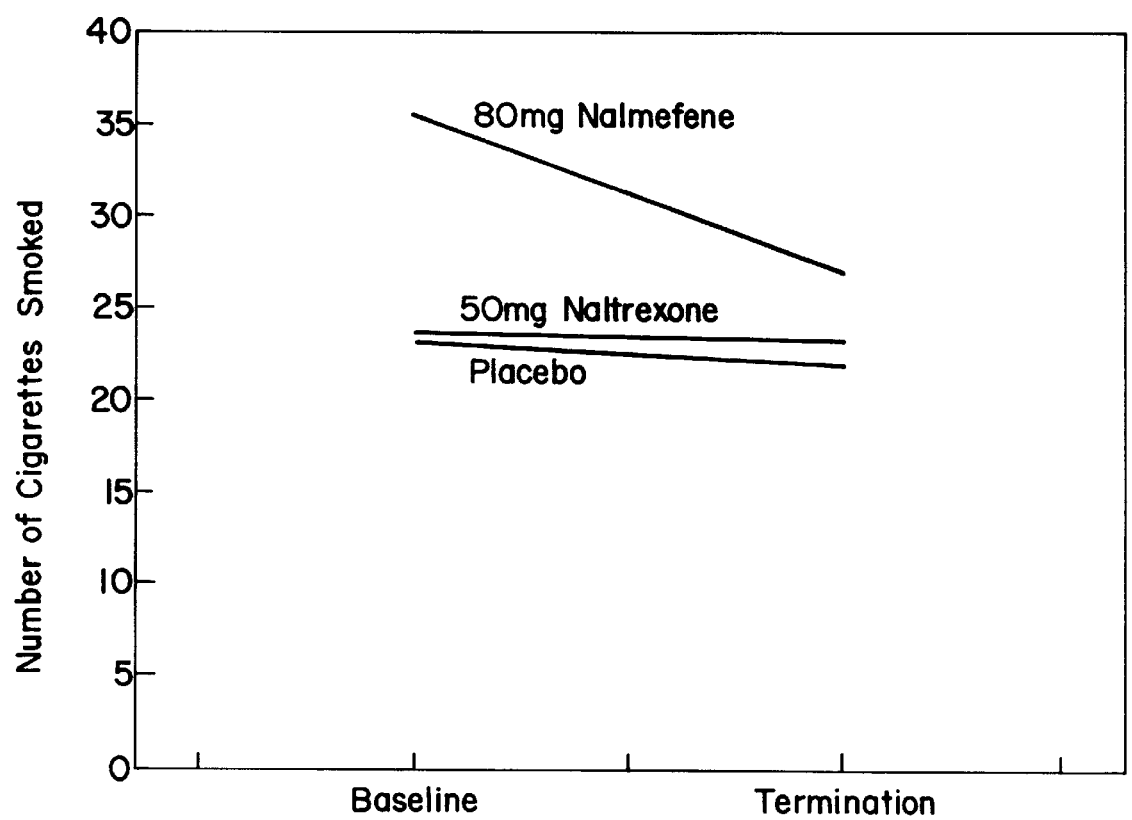
FIG. 1 is a graph reflecting the number of cigarettes smoked by three groups of subjects studied for twelve weeks: one group receiving 80 mg of nalmefene daily, a second group receiving 50 mg of naltrexone daily and a third group receiving a placebo.

The present invention resulted from the unexpected and surprising observation that patients being studied in a clinical trial of nalmefene for alcohol dependence and who were also smokers spontaneously decreased to a significant degree the number of cigarettes they smoked, while patients in another study receiving naltrexone for alcohol dependence exhibited virtually no decrease in cigarette consumption. This finding was contrary to expectations because nalmefene and naltrexone both bind primarily with the mu receptor in the brain and the two antagonists are very closely related in chemical structure; nalmefene is 6-desoxy-6-methylene naltrexone.

In accordance with the method of the invention, human subjects afflicted with (i.e., suffering from or exhibiting the symptoms and patterns of) nicotine dependence, whether in the form of persistent cigarette smoking, cigar or pipe smoking, tobacco chewing or any other form, are treated for their dependence through the administration of a daily dosage amount of about 10 to 300 mg of nalmefene, and preferably 20 to 100 mg, for about seven days to one year. The daily dosage amount may be administered in one to three equally divided doses.

Subjects suffering from severe nicotine dependency, including such behaviors as multiple attempts to quit smoking, smoking within thirty minutes of awakening in the morning, etc., may require the higher levels of daily dosage, up to 300 mg of nalmefene daily. In general, the length of the course of treatment in accordance with the invention will depend on the severity of nicotine dependency, the observed clinical response and the history of relapse.

The nalmefene is preferably administered to the subjects orally so that the subjects can self-medicate safely and conveniently. Nalmefene is highly effective and substantially available when administered orally. Oral dosage forms of nalmefene may include conventional tablets, capsules, caplets, pills, liquids (solutions, suspensions or elixirs) and the like, including generally about 0.5–80.0 mg of nalmefene per dosage unit together with suitable pharmaceutically-acceptable excipients, binders, sweeteners, coloring agents and other conventional additives.

Although the oral route of administration is preferred, for purposes of the invention the nalmefene may be administered parenterally or by any other conventional means for administering active pharmaceutical agents, for example, via transmucosal or transdermal administration.

Parenteral dosage forms may include conventional injectable solutions of nalmefene, for example, isotonic saline solutions, together with pharmaceutically acceptable buffers and preservatives. The parenteral dosage forms generally contain from about 0.5 to about 80.0 mg of nalmefene per dosage unit and may be injected by the subcutaneous, intramuscular or intravenous routes.

Suitable transmucosal and transdermal dosage forms may include known sublingual, buccal and intranasal vehicles, as well as patches and topical vehicles containing penetrants which enhance transdermal absorption of nalmefene. Examples of such transmucosal and transdermal vehicles may be found throughout the pharmaceutical literature, including in *Remington's Pharmaceutical Sciences,* 17th edition (1985).

Although there have been few reports of any significant adverse effects resulting from the administration of nalmefene daily dosage levels proposed by the present invention, if a subject is known to have had adverse reaction to nalmefene or a related opiate antagonist in the past or if it is suspected that the subject will exhibit an adverse reaction, the initial dosage of nalmefene administered can begin at a relatively low level, for example, daily doses of about 1.0 to about 20.0 mg for a limited period of time, e.g., one week, with gradual increments in the daily dosage of about 1 to about 20 mg in succeeding periods until the desired maintenance level is reached. This regimen should help the subject develop tolerance to any potential adverse effects.

In general, the present invention is not dependent on any particular vehicle or pharmaceutical composition or any particular route of administration. Any known method for getting effective treatment amounts of nalmefene into the bloodstream of the nicotine dependent subject may be utilized.

The following example demonstrates the efficacy of the method of the invention. This example is not intended, however, to limit or restrict the scope of the invention in any way and should not be construed as providing dosage forms, amounts or methods of administration which must be utilized exclusively to practice the invention.

All journal articles, texts, and patents cited in this specification are incorporated herein by reference in their entirety.

EXAMPLE

Two 12-week clinical studies of opiate antagonist treatment of alcohol dependence were conducted: (1) A double-blind placebo-controlled trial that included an 80 mg nalmefene treatment condition and a placebo treatment condition, and (2) an open-label safety study of naltrexone for the treatment of alcohol dependence. Both studies included weekly evaluations of drinking and any adverse drug events.

Additionally, subjects were asked to complete weekly self reports of behaviors the investigators believed to be potentially mediated by the endogenous opiate system, e.g., consumption of sweets, caffeine, or nicotine; frequency of sexual activity, exercise, television watching, etc. The purpose of the self reports was to determine whether chronic treatment of alcoholism with opiate antagonists resulted in unintended behavioral consequences. Subjects were not asked about these behaviors, nor were they addressed in their weekly alcoholism psychotherapy sessions. Higher smoking quit rates may be obtained when somatic treatment is combined with behavioral treatment than when either treatment is used alone (Fiore et al., J. Am. Med. Assoc., 271:1940–1947, 1994). Behavioral treatments are also described in Hurt et al. (Alcoholism Clin. Exp. Res., 18:867–872, 1994; J. Am. Med. Assoc., 271:595–600, 1994).

All subjects met DSM-III-R criteria for alcohol dependence. Additionally, 8 placebo, 11 nalmefene, and 4 naltrexone patients also met DSM III-R criteria for nicotine dependence, and were smoking an average of 23.3, 35.4 and 23.8 cigarettes per day, respectively, at the time of study entry. The only non-alcohol behavior studied that showed a clinically significant change from baseline at the time of study termination was daily cigarette consumption in the 80 mg nalmefene treatment group (a reduction in smoking of nearly half a pack a day), but not in the naltrexone or placebo treatment groups. The level of cigarette consumption remained unchanged from baseline in the placebo (t=0.21, df=10, p<0.9) and naltrexone groups (t=0.28, df=8, p<0.8). However, despite smoking more than the placebo and naltrexone groups at baseline, and receiving no behavioral treatment directed at smoking cessation, the nalmefene groups decreased their average number of cigarettes by 8.4 per day at the time of study termination (t=1.46, df=11, p<0.2) (see FIG. 1 and Table 1).

In keeping with published data linking mild appetite suppression with administration of opiate antagonists, patients who decreased cigarette smoking over the 12-week nalmefene treatment period showed mild weight loss (approximately one pound, on average) as opposed to the weight gain traditionally associated with smoking cessation (see Tables 2 and 3). Thus, the unique pharmacodynamic properties of nalmefene result in an effective medication for the treatment of nicotine dependence, particularly in patients concerned about weight gain. Consistent with prior clinical studies of nalmefene, the drug was well tolerated and no serious adverse drug events occurred.

TABLE 1

WITHIN GROUP CHANGE IN CIGARETTES PER DAY

| Variable | Mean | SD | t | df | P |
|---|---|---|---|---|---|
| Placebo | | | | | |
| cigs/day start | 23.2727 | 20.199 | | | |
| cig/day end | 21.9091 | 25.692 | .21 | 10 | .839 |
| 80 mg Nalmefene | | | | | |
| cigs/day start | 35.4167 | 23.008 | | | |
| cig/day end | 27.0000 | 20.401 | 1.46 | 11 | .172 |
| 50 mg Naltrexone | | | | | |
| cigs/day start | 23.7778 | 15.006 | | | |
| cig/day end | 23.0000 | 18.262 | .28 | 8 | .785 |

TABLE 2

SMOKERS BETWEEN GROUP WEIGHT CHANGE

| Variable | Number of cases | Mean | SD | t-value | df | 2-tail Sig |
|---|---|---|---|---|---|---|
| Placebo | 8 | −.8750 | 4.357 | | | |
| 80 mg Nalmefene | 11 | −.9545 | 7.370 | .03 | 17 | .979 |
| Placebo | 8 | −.8750 | 4.357 | | | |
| Naltrexone 80 mg | 4 | −5.7500 | 14.863 | .89 | 10 | .393 |
| Nalmefene | 11 | −.9545 | 7.370 | | | |
| Naltrexone | 4 | −5.7500 | 14.863 | .85 | 13 | .409 |

TABLE 3

SMOKERS WITHIN GROUP WEIGHT CHANGE

| Variable | Mean | SD | t-value | df | 2-tail Sig |
|---|---|---|---|---|---|
| PLACEBO | | | | | |
| Weight at Baseline | 144.1250 | 30.159 | | | |
| Weight at End | 143.2500 | 29.021 | .57 | 7 | .588 |
| 80 mg Nalmefene | | | | | |
| Weight at Baseline | 182.1818 | 36.780 | | | |
| Weight at End | 181.2727 | 38.792 | .41 | 10 | .692 |
| 50 mg Nalmefene | | | | | |
| Weight at Baseline | 152.0000 | 35.071 | | | |
| Weight at End | 146.2500 | 44.395 | .77 | 3 | .495 |

I claim:

1. A method of treating a human subject afflicted with nicotine dependence comprising administration of nalmefene to decrease the nicotine dependence of the human subject.

2. The method of claim 1, wherein the human subject does not gain weight as a result of decreased dependence on nicotine.

3. The method of claim 1, wherein nalmefene is administered daily.

4. The method of claim 1, wherein between about 10 mg to 300 mg of nalmefene is administered daily.

5. The method of claim 1, wherein between about 1 mg to 20 mg of nalmefene is administered daily.

6. The method of claim 1, wherein nalmefene is administered for a period of between about seven days to one year.

7. The method of claim 1, wherein nalmefene is administered orally.

8. The method of claim 1, wherein nalmefene is administered transmucosally or transdermally.

9. The method of claim 1, further comprising stopping administration of nalmefene to the subject to determine whether nicotine dependence of the human subject has decreased.

10. A method of treating a human subject afflicted with nicotine dependence comprising:
   (a) administering nalmefene to the human subject afflicted with nicotine dependence,
   (b) administering nicotine to the afflicted human subject while the nalmefene is blocking stimulation of opiate receptors in the human subject afflicted with nicotine dependence, and
   (c) repeating steps (a) and (b) until the human subject's dependence on nicotine is decreased.

11. The method of claim 10, wherein the human subject does not gain weight as a result of decreased dependence on nicotine.

12. The method of claim 10, wherein nalmefene is administered daily.

13. The method of claim 10, wherein between about 10 mg to 300 mg of nalmefene is administered daily.

14. The method of claim 10, wherein between about 1 mg to 20 mg of nalmefene is administered daily.

15. The method of claim 10, wherein nalmefene is administered for a period of between about seven days to one year.

16. The method of claim 10, wherein nalmefene is administered orally.

17. The method of claim 10, wherein nalmefene is administered transmucosally or transdermally.

18. The method of claim 10, further comprising stopping administration of nalmefene to the human subject to determine whether nicotine dependence of the subject has decreased.

19. A method of treating a human subject afflicted with nicotine dependence comprising administration of an opiate antagonist to decrease the nicotine dependence of the human subject, wherein the opiate antagonist is naltrexone and wherein the subject does not gain substantial weight as a result of decreased dependence on nicotine.

* * * * *

UNITED STATES PATENT AND TRADEMARK OFFICE
CERTIFICATE OF CORRECTION

PATENT NO. : 5,852,032
DATED : December 22, 1998
INVENTOR(S) : Mason, Barbara

It is certified that error appears in the above-identified patent and that said Letters Patent is hereby corrected as shown below:

Col. 1, after line 5, please insert the following:

This invention was made with government support under AA09560, awarded by the National Institutes on Alcohol Abuse and Alcoholism. The government has certain rights in the invention.

Signed and Sealed this

Twenty-second Day of February, 2000

Attest:

Q. TODD DICKINSON

*Attesting Officer*                *Commissioner of Patents and Trademarks*